United States Patent
Mashak et al.

(10) Patent No.: US 7,971,589 B2
(45) Date of Patent: Jul. 5, 2011

(54) SYSTEM AND METHOD FOR A COLLAPSIBLE RESERVOIR WITH AN AUXILLARY FLUID CHANNEL

(75) Inventors: James N. Mashak, Sun Prairie, WI (US); Robert Q. Tham, Middleton, WI (US)

(73) Assignee: General Electric Company, Schenectady, NY (US)

( * ) Notice: Subject to any disclaimer, the term of this patent is extended or adjusted under 35 U.S.C. 154(b) by 804 days.

(21) Appl. No.: 11/688,576

(22) Filed: Mar. 20, 2007

(65) Prior Publication Data

US 2008/0230059 A1 Sep. 25, 2008

(51) Int. Cl.
*A61M 16/00* (2006.01)
(52) U.S. Cl. .............. 128/205.13; 128/200.24
(58) Field of Classification Search ........... 128/205.13–205.17, 203.28, 200.22; 604/37, 23, 26, 98.01, 98.02, 185, 212, 257; 417/479, 480
See application file for complete search history.

(56) References Cited

U.S. PATENT DOCUMENTS

| | | | | |
|---|---|---|---|---|
| 50,735 A * | 10/1865 | Russell | ..................... | 128/200.12 |
| 339,821 A * | 4/1886 | Sutton | ........................... | 604/185 |
| 3,009,459 A * | 11/1961 | Ruben | ..................... | 128/205.13 |
| 3,046,978 A * | 7/1962 | Lea | ........................... | 128/205.13 |
| 3,063,620 A * | 11/1962 | Black | ............................ | 417/478 |
| 3,090,380 A * | 5/1963 | Dold | ....................... | 128/205.13 |
| 3,196,866 A * | 7/1965 | Adams | ..................... | 128/205.13 |
| 3,262,446 A * | 7/1966 | Stoner | ....................... | 128/205.13 |
| 3,356,100 A * | 12/1967 | Seeler | ........................... | 137/102 |
| 3,467,092 A * | 9/1969 | Bird et al. | ................. | 128/204.25 |
| 4,109,651 A * | 8/1978 | Steigerwald | ............. | 128/205.17 |
| 4,405,321 A * | 9/1983 | Budoff | ........................... | 604/212 |
| 4,498,472 A * | 2/1985 | Tanaka | ....................... | 128/205.17 |
| 4,502,481 A * | 3/1985 | Christian | ................. | 128/205.24 |
| 4,532,923 A * | 8/1985 | Flynn | ....................... | 128/205.13 |
| 4,539,985 A * | 9/1985 | Magrath | ................... | 128/205.13 |
| 4,821,712 A * | 4/1989 | Gossett | ..................... | 128/205.15 |
| 5,222,491 A * | 6/1993 | Thomas | ................... | 128/205.13 |
| 5,297,944 A * | 3/1994 | Pomeroy | ........................ | 417/437 |
| 6,578,574 B1 * | 6/2003 | Køhnke | ..................... | 128/203.11 |
| 6,938,618 B2 * | 9/2005 | Lurie et al. | ................ | 128/205.24 |
| 2006/0180146 A1 * | 8/2006 | Thompson et al. | ....... | 128/202.28 |

FOREIGN PATENT DOCUMENTS

WO WO 2006/119515 11/2006

OTHER PUBLICATIONS

"Non-Rebreathing Systems," A.M. Bickford Inc.. http://www.ambickford.com/bick4.html.
GB Search Report dated Jun. 9, 2008.

* cited by examiner

*Primary Examiner* — Justine R Yu
*Assistant Examiner* — LaToya M Louis
(74) *Attorney, Agent, or Firm* — Andrus, Sceales, Starke & Sawall, LLP

(57) ABSTRACT

A collapsible reservoir system is disclosed herein. The collapsible reservoir system includes a first tube pneumatically connected to the collapsible reservoir, and a second tube pneumatically connected to the collapsible reservoir. The second tube is configured to generally remain open in the absence of an externally applied compressive force. The second tube is positioned relative to the collapsible reservoir such that a compressive force applied to the collapsible reservoir can also compress and thereby restrict the second tube. A corresponding method for controlling the pressure of a collapsible reservoir system is also provided.

20 Claims, 1 Drawing Sheet

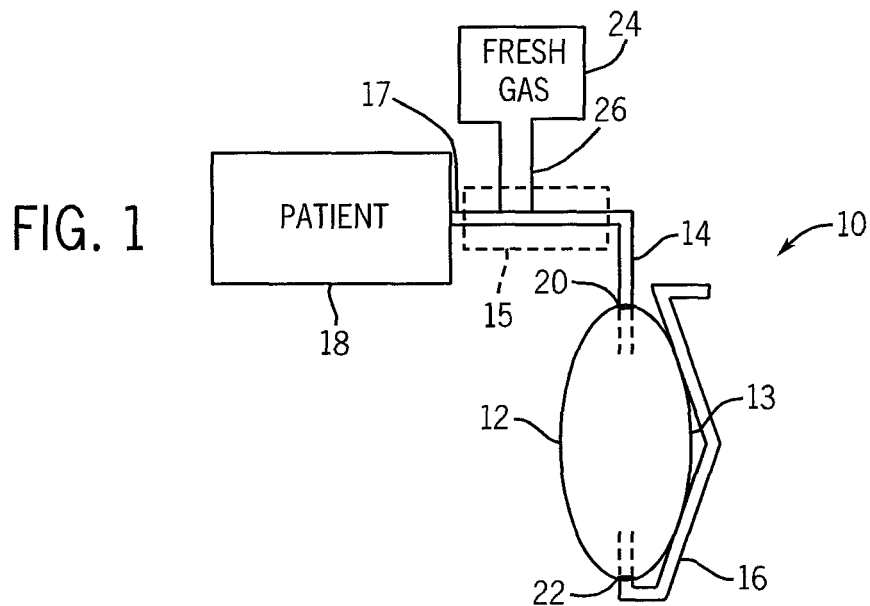
FIG. 1
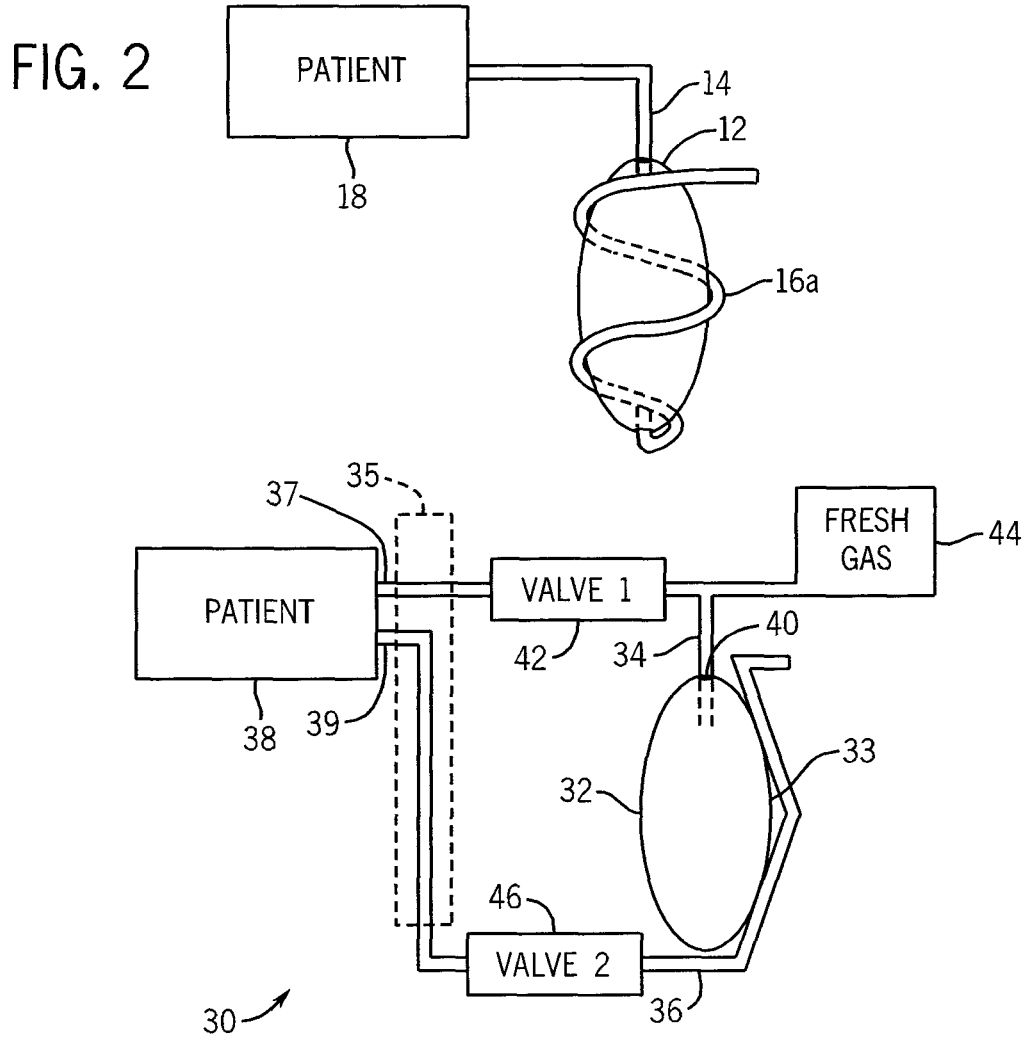
FIG. 2
FIG. 3

SYSTEM AND METHOD FOR A COLLAPSIBLE RESERVOIR WITH AN AUXILLARY FLUID CHANNEL

FIELD OF THE INVENTION

This disclosure relates generally to a collapsible reservoir to store and control the delivery of fluid. As medical device, it can be use as a resuscitation system or in conjunction with a medical ventilator system to manually augment patient breathing.

BACKGROUND OF THE INVENTION

In general, medical ventilator systems are used to provide respiratory support to patients undergoing anesthesia and respiratory treatment whenever the patient's ability to breath is compromised. The primary function of the medical ventilator system is to maintain suitable pressure and flow of gases inspired and expired by the patient. Medical ventilator systems used in conjunction with anesthesia generally include an automatic system comprising a bellows and a manual system comprising a collapsible reservoir configured to allow a clinician to deliver manual breaths to the patient.

The manual system is implemented to ventilate a patient by repeatedly compressing and releasing the collapsible reservoir. When the collapsible reservoir is compressed, inhalation gas is transferred to the patient. When the collapsible reservoir is subsequently released, the patient passively exhales due to the lungs' elasticity. Fresh gas is generally continuously introduced into the system, and at least a portion of the patient's exhaled gas can be recycled and transferred back to the patient. A pressure release valve is traditionally provided to limit the pressure level in the manual system and thereby regulate the volume of inhalation gas transferred to the patient during each compression of the collapsible reservoir.

As an operator compresses and releases the collapsible reservoir to manually ventilate a patient, her or she typically must also operate the pressure release valve in order to maintain optimal ventilator system performance. The operation of the pressure release valve must be coordinated with the compression and release of the collapsible reservoir. For example, an operator may have to constantly adjust the pressure release valve between a low relief pressure setting for spontaneous only breathing, and a higher pressure setting to enable augmented positive pressure synchronous with patient inhalation. The problem is that the operation of the pressure release valve in the manner described unnecessarily burdens the operator and is also subject to operator error.

BRIEF DESCRIPTION OF THE INVENTION

The above-mentioned shortcomings, disadvantages and problems are addressed herein which will be understood by reading and understanding the following specification.

In an embodiment, a collapsible reservoir system includes a collapsible reservoir, a first tube pneumatically connected to the collapsible reservoir, and a second tube pneumatically connected to the collapsible reservoir. The second tube is configured to generally remain open in the absence of an externally applied compressive force. The second tube is positioned relative to the collapsible reservoir such that a compressive force applied to the collapsible reservoir can also compress and thereby restrict the second tube.

In another embodiment, a collapsible reservoir system includes a first tube that is pneumatically connectable to an inlet hose of a patient circuit, a collapsible reservoir that is pneumatically connectable to the first tube, and a second tube that is pneumatically connectable to an outlet hose of the patient circuit. The second tube is configured to generally remain open in order to release excess pressure from the collapsible reservoir system. The second tube is also configured to automatically occlude when a compressive force is applied to the collapsible reservoir.

In another embodiment, a method for controlling the pressure of a collapsible reservoir system includes providing a collapsible reservoir in fluid communication with a patient circuit, providing a first tube in fluid communication with the patient circuit, and providing a second tube in fluid communication with the patient circuit. The method also includes compressing the collapsible reservoir and generally simultaneously compressing the second tube such that the second tube becomes occluded and at least a portion of the contents of the collapsible reservoir are transferred to the patient circuit. The method also includes releasing the collapsible reservoir after the collapsible reservoir has been compressed. Wherein releasing the collapsible reservoir also opens the second tube such that excess pressure in the collapsible reservoir system can be released therethrough.

Various other features, objects, and advantages of the invention will be made apparent to those skilled in the art from the accompanying drawings and detailed description thereof.

BRIEF DESCRIPTION OF THE DRAWINGS

FIG. 1 is a schematic diagram of a collapsible reservoir system in accordance with an embodiment;

FIG. 2 is a schematic diagram of a collapsible reservoir system in accordance with another embodiment; and FIG. 3 is a schematic diagram of a collapsible reservoir system in accordance with another embodiment.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Referring to FIG. 1, a collapsible reservoir system 10 is schematically depicted in accordance with an embodiment. The collapsible reservoir system 10 may, for example, be implemented as a component of a medical ventilator system (not shown). The collapsible reservoir system 10 includes a collapsible reservoir 12, a first tube 14 and a second tube 16. It should be appreciated that the second tube 16 may include one or more tubes. The collapsible reservoir system 10 will hereinafter be described in accordance with the exemplary embodiment depicted in FIG. 1 wherein the first tube 14 is configured to transfer gas to and receive gas from a patient 18, and the second tube 16 is an exhaust tube configured to release gas to atmosphere or transfer it to a scavenging system (not shown). It should, however, be appreciated that the first tube 14 and the second tube 16 may be configured for alternate purposes.

According to the exemplary embodiment of FIG. 1, the collapsible reservoir system 10 is operatively connected to a patient circuit 15 configured to transfer gas to and from the patient 18. The patient circuit 15 is pneumatically connected to a single inlet/outlet hose 17 through which the patient 18 can inhale and exhale. The patient circuit 15 is a "semi-open circuit" such as a Bain circuit, or a "semi-closed circuit" such as a "water to and fro circuit" wherein gas exhaled by the patient 18 is transferable to the collapsible reservoir 12, and can thereafter be re-circulated from the collapsible reservoir 12 back to the patient 18. The first tube 14 is pneumatically connected to the inlet/outlet hose 17 via the patient circuit 15. A fresh gas supply 24 that is constrained to one-way flow replenishes oxygen consumed by the patient 18. A conduit 26 pneumatically connects the fresh gas supply 24 to the patient circuit 15. While it is preferable that conduit 26 be connected to the patient circuit 15 via a pneumatic coupling proximal to the inlet/outlet hose 17, this connection can be made anywhere along the patient gas breathing passage including a direct pneumatic coupling to the tube 14 or the inlet/outlet hose 17. Similarly, the collapsible reservoir 12 can be pneumatically connected to work with a more sophisticated configuration of the patient circuit 15, such as a "circle breathing circuit" commonly used in anesthesia machines. For purposes of this disclosure, the terms "pneumatic connection" and "pneumatic coupling" are defined in a non-limiting manner to include an attachment of two or more components that is adapted to facilitate the transmission of a gas between or through the attached components.

The collapsible reservoir 12 generally comprises a pliable bladder or bag that is repeatedly compressed and released in order to manually ventilate a patient. The collapsible reservoir 12 is commonly referred to as a hand bag, and is so named because an operator typically uses his or her hand to compress and release the collapsible reservoir 12. The collapsible reservoir 12 includes a first opening 20 configured to pneumatically couple the collapsible reservoir 12 with the first tube 14 such that the first tube 14 is in fluid communication with the collapsible reservoir 12. The collapsible reservoir 12 also includes a second opening 22 configured to pneumatically couple the collapsible reservoir 12 with the second tube 16 such that the second tube 16 is in fluid communication with the collapsible reservoir 12. For purposes of this disclosure, the term "fluid" is defined to include any continuous, amorphous substance whose molecules move freely past one another and that has the tendency to assume the shape of its container. Accordingly, a "fluid" may include a liquid or a gas.

The second tube 16 is comprised of a pliable material that can be manually compressed to restrict fluid flow therethrough. At least a portion of the second tube 16 is in contact with or in close proximity to an outer surface 13 of the collapsible reservoir 12. Therefore, when an operator squeezes the collapsible reservoir 12 in order to manually ventilate the patient 18, the operator is also likely to engage and thereby restrict the second tube 16.

According to one embodiment, the second tube 16 is secured directly to the outer surface 13 of the collapsible reservoir 12, and extends generally along the length of the collapsible reservoir 12. Advantageously, this configuration extends the contact region for the second tube 16 such that an operator does not need to find a specific point of contact in order to operate the device. According to another embodiment, the second tube 16 is disposed about the periphery of the collapsible reservoir 12 in a pattern adapted to increase the likelihood that the second tube 16 will be engaged during collapsible reservoir 12 compression. For example, with reference to FIG. 2, it can be seen that by disposing a second tube 16*a* about the periphery of the collapsible reservoir 12 in a generally spiraled pattern, an operator can engage the second tube 16*a* regardless of the orientation at which his or her hand (not shown) approaches the collapsible reservoir 12.

According to the exemplary embodiment of FIG. 1, the second tube 16 remains open in the absence of an externally applied force such as, for example, a compressive force applied by an operator's hand (not shown). Allowing the second tube 16 to generally remain open in the manner described prevents the accumulation of excess pressure in the collapsible reservoir system 10. This operational mode of the second tube 16 functionally replaces a more conventional pressure release valve.

When an operator generally simultaneously squeezes both the collapsible reservoir 12 and the second tube 16, the second tube 16 becomes occluded in response to the external force applied by the operator's hand (not shown) such that all or most of the contents of the collapsible reservoir 12 are directed to the patient 18. When the collapsible reservoir 12 is subsequently released the patient 18 passively exhales due to the elasticity of his or her lungs. The act of releasing the collapsible reservoir 12 also releases and thereby opens the second tube 16 such that any excess pressure can be released therethrough. According to one embodiment, a backpressure can be exerted to keep the collapsible reservoir 12 inflated. Such backpressure can be exerted by the flow restriction provided by the second tube 16, or by an optional valve (not shown) which is well known to those skilled in the art, in order to provide positive end expiratory pressure (PEEP). The exhaled gas from the patient's lungs is transferred back to the collapsible reservoir 12 where it may be recycled during a subsequent collapsible reservoir 12 compression or exhausted through the second tube 16.

A primary purpose of the collapsible reservoir system 10 is to transfer a desired quantity of gas to the patient 14 as a means for providing respiratory support and/or anesthesia. Closing the second tube 16 during collapsible reservoir 12 compression is critical to the operation of the collapsible reservoir system 10. As an example, if the second tube 16 remained open during collapsible reservoir 12 compression, gas within the collapsible reservoir 12 could escape through the exhaust system thereby interrupting the transfer of gas to the patient 14 and defeating the primary purpose of the collapsible reservoir system 10. By providing the second tube 16 configured in the manner previously described, the collapsible reservoir system 10 can effectively provide respiratory support and/or anesthesia without accumulating excess pressure. It should also be appreciated that the collapsible reservoir system 10 having a second tube 16 that automatically opens and closes is easier to operate than conventional collapsible reservoir systems incorporating a pressure release valve that must be manually opened and closed in a coordinated manner.

Referring to FIG. 3, a collapsible reservoir system 30 is schematically depicted in accordance with an embodiment. The collapsible reservoir system 30 may, for example, be implemented as a component of a medical ventilator system (not shown). The collapsible reservoir system 30 includes a collapsible reservoir 32, a first tube 34 and a second tube 36. It should be appreciated that the second tube 36 may include one or more tubes. The collapsible reservoir system 30 will hereinafter be described in accordance with the exemplary embodiment depicted in FIG. 3 wherein the first tube 34 is configured to transfer gas to and receive gas from a patient 38, and the second tube 36 is an exhaust tube configured to release gas to atmosphere or transfer it to a scavenging system (not shown). It should, however, be appreciated that the first tube 34 and the second tube 36 may be configured for alternate purposes.

According to the exemplary embodiment of FIG. 3, the collapsible reservoir system 30 is operatively connected to a patient circuit 35 configured to transfer gas to and from the patient 38. The patient circuit 35 is pneumatically connected to an inlet hose 37 through which the patient 38 can inhale and an outlet hose 39 through which the patient 38 can exhale. The first tube 34 is pneumatically connected to the inlet hose 37 via the patient circuit 35, and the second tube 36 is pneumatically connected to the outlet hose 39 via the patient circuit 35.

The collapsible reservoir 32 generally comprises a pliable bladder or bag that is repeatedly compressed and released in order to manually ventilate a patient. The collapsible reservoir 32 includes an opening 40 configured to pneumatically couple the collapsible reservoir 32 with the first tube 34 such that the first tube 34 is in fluid communication with the collapsible reservoir 32.

The second tube 36 is comprised of a pliable material that can be manually compressed to restrict fluid flow therethrough. At least a portion of the second tube 36 is in contact with or in close proximity to an outer surface 33 of the collapsible reservoir 32. Therefore, when an operator squeezes the collapsible reservoir 32 in order to manually ventilate the patient 38, the operator is also likely to engage and thereby restrict the second tube 36.

According to one embodiment, the second tube 36 is secured directly to the outer surface 33 of the collapsible reservoir 32, and extends generally along the length of the collapsible reservoir 32. Advantageously, this configuration extends the contact region for the second tube 36 such that an operator does not need to find a specific point of contact in order to operate the device. According to another embodiment, the second tube 36 may be disposed about the periphery of the collapsible reservoir 32 in a manner similar to that of the second tube 16a (shown in FIG. 2) in order to increase the likelihood that the second tube 36 will be engaged during collapsible reservoir 32 compression.

The second tube 36 operates similarly to the previously described second tube 16 (shown in FIG. 1). More precisely, the second tube 36 generally remains open in the absence of an externally applied force and is adapted to close when an operator compresses the collapsible reservoir 32 in a manner similar to that described in detail hereinabove with respect to the second tube 16.

When an operator generally simultaneously squeezes both the collapsible reservoir 32 and the second tube 36, the second tube 36 becomes occluded in response to the external force applied by the operator's hand (not shown) such that all or most of the contents of the collapsible reservoir 32 are directed to the patient 38. When the collapsible reservoir 32 is subsequently released the patient 38 passively exhales due to the elasticity of his or her lungs. The act of releasing the collapsible reservoir 32 also releases and thereby opens the second tube 36 such that gas exhaled from the patient's lungs is transferred therethrough. The exhaled gas in the second tube 36 may, for example, be released to atmosphere or may be directed to a scavenger system (not shown).

The collapsible reservoir system 30 may also include a first valve 42 and a fresh gas supply 44 that are both operatively connected to the first tube 34. The first valve 42 may comprise a check valve configured to restrict fluid flow from the patient back to the collapsible reservoir 32. The first valve 42 may also be configured to provide a selectable amount of resistance within the first tube 34 in order to ensure the collapsible reservoir 32 remains inflated with gas from the fresh gas supply 44. According to one embodiment, the fresh gas supply 44 is configured to deliver gas at a higher pressure level than that which is attainable by squeezing the collapsible reservoir 32 such that gas from the collapsible reservoir 32 is prevented from entering the fresh gas supply 44. The patient 38 can spontaneously inhale and thereby draw gas from the fresh gas supply 44 and the collapsible reservoir 32. The collapsible reservoir system 30 can also include a second valve 46 operatively connected to the second tube 36. The second valve 46 is optional and may be implemented to provide positive-end expiratory pressure (PEEP).

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A collapsible reservoir system comprising:
   a manually collapsible reservoir filled with gas;
   a first tube pneumatically connected to the manually collapsible reservoir; and
   a manually collapsible second tube pneumatically connected and continuously open to the manually collapsible reservoir, said second tube configured to generally remain open in the absence of an externally applied compressive force, said second tube being positioned relative to the collapsible reservoir such that a manual compressive force applied to the collapsible reservoir simultaneously compresses and thereby restricts the second tube to increase the back pressure within the manually collapsible reservoir to direct gas from the reservoir through the first tube.

2. The collapsible reservoir system of claim 1, wherein the second tube extends generally along the length of the collapsible reservoir such that an operator can engage the second tube at a plurality of different locations and does not need to find a specific point of contact in order to restrict the second tube.

3. The collapsible reservoir system of claim 1, wherein at least a portion of the second tube is secured to an outer surface of the collapsible reservoir to increase the likelihood that a compressive force applied to the collapsible reservoir will also compress and thereby restrict the second tube.

4. The collapsible reservoir system of claim 1, wherein at least a portion of the second tube is disposed in close proximity to an outer surface of the collapsible reservoir to increase the likelihood that a compressive force applied to the collapsible reservoir will also compress and thereby restrict the second tube.

5. The collapsible reservoir system of claim 1, wherein at least a portion of the second tube is disposed about the periphery of the collapsible reservoir in a generally spiraled pattern to increase the likelihood that a compressive force applied to the collapsible reservoir will also compress and thereby restrict the second tube.

6. The collapsible reservoir system of claim 1, wherein the second tube comprises a reservoir end physically connected to the manually collapsible reservoir, and a free end that opens to the exterior of the reservoir.

7. The collapsible reservoir system of claim 6, wherein the second tube is an exhaust tube configured to release excess pressure from the collapsible reservoir system.

8. A collapsible reservoir system comprising:
   a first tube pneumatically connected to an inlet hose of a patient circuit;

a manually collapsible reservoir pneumatically connected to the first tube; and a second tube pneumatically connected and continuously open to an outlet hose of the patient circuit;

wherein the second tube is configured to generally remain open in order to release excess pressure to the exterior of the collapsible reservoir system, and wherein at least a portion of the second tube is integral with the manually collapsible reservoir such that a manual compressive force applied to the collapsible reservoir further occludes the second tube.

9. The collapsible reservoir system of claim 8, wherein the second tube comprises a plurality of tubes.

10. The collapsible reservoir system of claim 8, wherein the second tube extends generally along the length of the collapsible reservoir such that an operator can engage the second tube at a plurality of different locations and does not need to find a specific point of contact in order to restrict the second tube.

11. The collapsible reservoir system of claim 8, wherein at least a portion of the second tube is disposed in close proximity to an outer surface of the collapsible reservoir to increase the likelihood that a compressive force applied to the collapsible reservoir will also compress and thereby occlude the second tube.

12. The collapsible reservoir system of claim 8, wherein at least a portion of the second tube is disposed about the periphery of the collapsible reservoir in a generally spiraled pattern to increase the likelihood that a compressive force applied to the collapsible reservoir will also compress and thereby occlude the second tube.

13. The collapsible reservoir system of claim 8, further comprising a valve operatively connected to the first tube.

14. The collapsible reservoir system of claim 13, further comprising a fresh gas supply operatively connected to the first tube.

15. The collapsible reservoir system of claim 14, further comprising a second valve operatively connected to the second tube the second valve being adjustable to adjust the positive end expiratory pressure of the collapsible reservoir system.

16. A method for controlling the pressure of a collapsible reservoir system comprising;

providing a collapsible reservoir in fluid communication with a patient circuit;

providing a first tube in fluid communication with the patient circuit;

providing a second tube in fluid communication with the patient circuit;

compressing the collapsible reservoir and generally simultaneously compressing the second tube such that the second tube becomes occluded and creates a back pressure within the collapsible reservoir such that at least a portion of the contents of the collapsible reservoir are transferred to the patient circuit; and releasing the collapsible reservoir after said compressing the collapsible reservoir, wherein said releasing the collapsible reservoir also opens the second tube such that excess pressure in the collapsible reservoir system can be released therethrough.

17. The method of claim 16, wherein said compressing the collapsible reservoir and generally simultaneously compressing the second tube includes manually squeezing the collapsible reservoir and generally simultaneously manually squeezing the second tube.

18. The method of claim 16, wherein said providing a second tube includes providing a second tube that extends generally along the length of the collapsible reservoir such that an operator can engage the second tube at a plurality of different locations and does not need to find a specific point of contact in order to restrict the second tube.

19. The method of claim 16, wherein the second tube comprises a free end through which the excess pressure is released to the exterior of the collapsible reservoir system.

20. The method of claim 16, wherein said providing a second tube includes providing a second tube disposed about the periphery of the collapsible reservoir in a generally spiraled pattern.

* * * * *